United States Patent [19]

Mauro et al.

[11] Patent Number: 5,672,735
[45] Date of Patent: Sep. 30, 1997

[54] PROCESS FOR THE PREPARATION OF A DICARBOXYLIC ACID DI-CHLORIDE

[75] Inventors: Marina Mauro; Carlo Felice Viscardi; Massimo Gatti; Nicola Desantis, all of Mozzo, Italy

[73] Assignee: Fructamine S.p.A., Italy

[21] Appl. No.: 651,474

[22] Filed: May 21, 1996

[30] Foreign Application Priority Data

May 23, 1995 [IT] Italy .................................. MI95A1048
Aug. 4, 1995 [IT] Italy .................................. RM95A0548

[51] Int. Cl.$^6$ .......................... C07C 67/14; C07C 67/48
[52] U.S. Cl. .......................... 560/252; 560/248; 560/254
[58] Field of Search .......................... 560/248, 252, 560/254

[56] References Cited

U.S. PATENT DOCUMENTS

| | | | |
|---|---|---|---|
| 4,001,323 | 1/1977 | Felder et al. | 260/559 A |
| 4,139,605 | 2/1979 | Felder et al. | 424/5 |
| 4,364,921 | 12/1982 | Speck et al. | 424/5 |
| 5,362,905 | 11/1994 | Villa et al. | 560/250 |
| 5,550,287 | 8/1996 | Cannata et al. | 564/153 |

FOREIGN PATENT DOCUMENTS 2 271 990   5/1994   United Kingdom.

*Primary Examiner*—José G. Dees
*Assistant Examiner*—Rosalynd A. Williams
*Attorney, Agent, or Firm*—Nixon & Vanderhye

[57] ABSTRACT

The present invention refers to a Process for the preparation of S-(-)-5-[[2-(acetyloxy)-1-oxopropyl]amino]-2,4,6-triiodo-1,3-benzenedicarboxylic acid dichloride of formula (I) comprising the reaction between S-(-)-[2-(acetyloxy)] propionic acid chloride and 5-amino-2,4,6-triiodo-, 1,3-benzenedicarboxylic acid dichloride, in an aprotic dipolar solvent and in presence of a halogenhydric acid.

17 Claims, No Drawings

PROCESS FOR THE PREPARATION OF A DICARBOXYLIC ACID DI-CHLORIDE

This invention refers to a new process for the synthesis of S-5-[[2-(acetyloxy)-1-oxopropyl]amino]-2,4,6-triiodo-1,3-benzenedicarboxylic acid dichloride of formula (I).

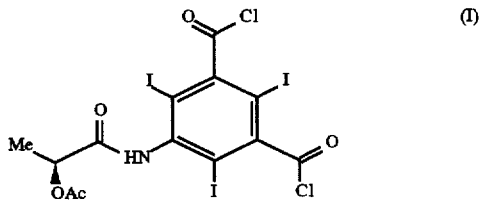

The compound of formula (I) has been previously described in patent GB 1472050 and used as intermediate for the synthesis of S-N,N'-bis[2-hydroxy-1-(hydroxymethyl)ethyl]-5-[(2-hydroxy-1-oxopropyl)amino]-2,4,6-triiodol,3-benzenedicarboxamide, from now on called Compound A.

The synthesis of the compound of formula (I) described in the above mentioned patent foresees the following reaction as in Scheme 1.

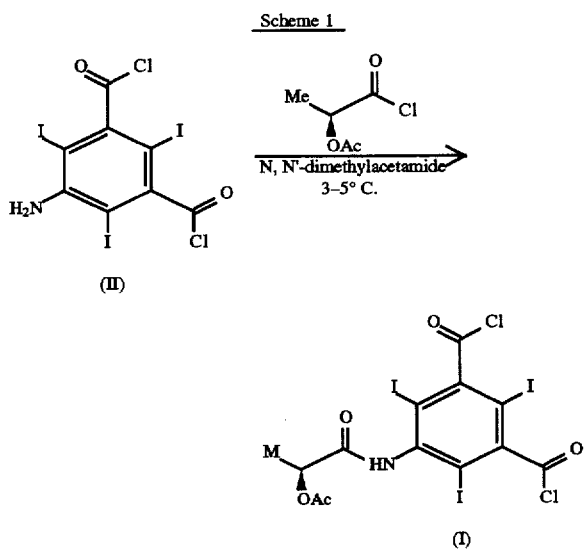

The reaction of 5-amino-2,4,6-triiodo-1,3-benzenedicarboxylic acid dichloride (compound of formula (II)) is carried out, according to GB 1472050, with 2.5 equivalents of S-(-)-[2-(acetyloxy)]propionic acid chloride, in dimethylacetamide at 3°–5° C.

Recently, patent application GB 2271990 has been published, which describes a process for the preparation of compound (I) characterized by the use, in the reaction of Scheme 1, of a Lewis acid in catalytic amounts. According to the authors, the improvement brought by the invention lies in the quantitative conversions. The reaction solvent can be varied thus avoiding the drawbacks deriving from the removal of dimethylacetamide.

As previously cited, Compound A is a product containing a chiral centre and whose pharmacopoeia standards (for instance USP XXV; FU IX ed.) indicate a specific minimum rotatory optical power ranging between $[\alpha]_{20}^{436} = -4.6°$ and $-5.2°$ (c=40, H$_2$O).

It has been found, and this is one of the aspects of this invention, that the reaction of the Scheme 1 when carried out in dimethylacetamide or in another aprotic dipolar solvent, in presence of an halogenhydric acid, leads to a reaction mixture containing an optical and chemical pure final product.

Furthermore, the present invention refers to a industrially convenient process for the purification of this reaction mixture, which leads to the pure product of formula (I) in high yield and with a specific rotatory optical power ranging between $[\alpha]_{20}^{D} = -13.7$ and $-14.7°$ (c=10, CH$_3$CN) and with a chemical purity better than 99%. Said product, used as intermediate in the synthesis of Compound A, leads to a contrast agent which meets the pharmacopoeia standards and particularly those referring to specific rotatory optical power.

Therefore, the scope of this invention is a process for the preparation of the compound of formula (I), which comprises the reaction between S-(-)-[2-(acetyloxy)]propionic acid chloride with the compound of formula (II), 5-amino-2,4,6-triiodo-,1,3-benzenedicarboxylic acid dichloride, in an aprotic dipolar solvent and in presence of a halogenhydric acid.

In a preferred embodiment of the invention the aprotic dipolar solvent is selected from the group consisting of N,N-dimethylacetamide, N,N-dimethylformamide and N-methyl-2-pyrrolidone, preferably N,N-dimethylacetamide.

Particularly preferred are the conditions of reaction, in which the halogenhydric acid is added as an anhydrous gas in a 0.1:3 molar ratio for the product of formula (II).

Equally preferred are the conditions of reaction under which the amount of halogenhydric acid is added as a salt of the above cited aprotic dipolar solvents. Particularly preferred is the dimethylacetamide hydrochloride.

Equally preferred are the conditions of reaction, under which the temperature ranges between 0° and 40° C.

This invention also refers to the process for the purification and isolation of S-5-[[2-(acetyloxy)-1-oxopropyl]amino]-2,4,6-triiodo-1,3-benzenedicarboxylic acid dichloride coming from the reaction of formation of the same.

It has been found that the dilution of the reaction mixture, containing the final product and the aprotic dipolar solvent, with a solvent selected from the group consisting of: acetic acid esters with linear or branched (C$_3$–C$_5$) alcohols; secondary or tertiary alcohols, linear or branched (C$_3$–C$_5$); mono-, di- or polychloro (C$_1$–C$_4$) alkanes, followed by addition of water allows the isolation of the desired product with excellent yield, the removal of the aprotic dipolar solvent in an easy and complete way, and gives a product which has all the necessary chemical-physical characteristics to carry out the synthesis of Compound A in accordance with pharmacopoeia standards.

This invention also refers to the process of purification and isolation of S-(-)-5-[[2-(acetyloxy)-1-oxopropyl]amino]-2,4,6-triiodo-1,3-benzenedicarboxylic acid dichloride, comprising the following steps:

the dilution of the reaction mixture with acetic acid esters with linear or branched (C$_3$–C$_5$) alcohols or mono-, di- or polychloro (C$_1$–C$_4$) alkanes in a ratio between the dilution solvent and the aprotic dipolar solvent of 0.3:1 to 2.5:1 w/w;

the extraction of the aprotic dipolar solvent with water in a ratio of water to the dilution solvent ranging from 0.5:1 to 4:1 w/w;

the precipitation of the product with water.

Particularly preferred are the solvents selected from propyl acetate, n-butyl acetate and methylchloroform.

It has been surprisingly found that the purification of the reaction mixture can be advantageously carried out by using an alternative method based on the use of a continuous extractor, fed by the same solvent used for the dilution of the reaction mixture and with water to the two ends and with the reaction mixture on an intermediate plate. The product is isolated by concentration of the solvent phase. Also in this case the product meets the desired chemical-physical standards of purity.

As far as the use of secondary or tertiary ($C_1$-$C_3$) linear or branched alcohols is concerned, the dilution can be performed either through the addition of the selected solvent to the reaction mixture, or by adding the reaction mixture to the hydroalcoholic solution containing the selected alcohol, always in a ratio of dilution solvent to the aprotic dipolar solvent present in the reaction mixture ranging from 0 to 1.5 w/w, preferably in a ratio ranging from 0.3 to 0.6 w/w.

The following examples of the practice of the present invention are meant to be illustrative and are in no way limiting the scope of the invention.

EXAMPLE 1

(S)-5-[[2-(acetyloxy)-1-oxopropyl]amino]-2,4,6-triiodo-1,3-benzenedicarboxylic acid dichloride.

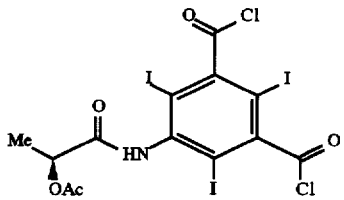

A) S-(-)-[2-(acetyloxy)]propionic acid sodium salt 560 g of S-(-)lactic acid sodium salt are dissolved in 1.5 kg of acetic acid. 180 g of HCl (35–38% w/w) and 650 g of acetic anhydride are added with stirring without exceeding a temperature of 40° C. The solution is cooled to 20° C. and 20 g of anhydrous sodium acetate are added with stirring for 30 min. The resulting suspension is filtered trough celite and the filter is washed with 50 g of acetic acid. The filtrate is concentrated by distillation under vacuum of a mixture formed by acetic acid-acetic anhydride (5–12% anhydride). The concentrate, corresponding to the desired product, is used as such in the successive step.

B) S-(-)-[2-(acetyloxy)]propionic acid chloride 640 g of technical $SOCl_2$ are dropwise added to the concentrate obtained through step A), at a temperature of 80° C. by keeping during this phase a temperature of 65°–70° C. At the end of the addition the exceeding $SOCl_2$ is eliminated via concentration under vacuum. The desired product is distilled at a temperature of 45°–70° C. and at a pressure of 11–15 mmHg. 677 g of said product are obtained.

Yield: 90%

Gas-chromatography: 99.5%

$[\alpha]_{20}^D$=−35.8° (on the product)

$^1$H-NMR, $^{13}$C-NMR, IR and MS spectra are consistent with the structure.

C) 5-amino-1,3-benzenedicarboxylic acid 325 g 5-nitro-1,3-benzenedicarboxylic acid (product available on the market) are loaded into a reactor with 2.8 l of water. It is heated to 60°–70° C. and the starting product dissolved by addition of 410 g of 30% NaOH. Then 10 g of charcoal are added; the slurry is filtered and the filter is washed with 200 ml of water.

8 g of Pd/C 5% (product available on the market) are then loaded and conditioned with approx. 0.01 m³ nitrogen. 0.1 m³ hydrogen are added under a pressure of 30 kPa. The temperature spontaneously reaches 50° C. and is kept by cooling. When the hydrogen consumption stops, the solution is kept under pressure for 1 h and then the residual hydrogen is removed by washing with 0.02 m³ of nitrogen. The suspension is filtered and the filter washed with 100 ml of water giving approx. 3.85 kg of solution containing 5-amino-1,3-benzenedicarboxylic acid sodium salt.

D) 5-amino-2,4,6-triiodo-1,3-benzenedicarboxylic acid

In a reactor loaded with 2.75 l of water, are added in sequence 0.08 kg of HCl (34% w/w), 3.85 kg of solution of 5-amino-1,3-benzenedicarboxylic acid sodium salt coming from the previous reaction and 375 g of $H_2SO_4$ (1:1 aqueous solution). The content is heated to 70° C., and during 3 hours 1.35 kg of a solution of ICl in HCl (44.5% iodine, molar ratio ICl:HCl=1:1) (product available on the market) is added. When the addition is complete the solution is heated to 90° C. and the temperature kept for 6 h. Then the content is cooled to 60° C. and transferred to another reactor, where it is cooled to 30° C. The slurry is decolourised by adding 45 g of sodium bisulfite under stirring, then centrifuged and the product washed with 0.3 kg of water thus giving 935 g of the desired wet product. After drying, 830 g of the desired product are obtained.

Total yield of the two steps (on the anhydrous product): 95.0%

Water content: 2%

Potentiometric assay: 99.3%

$^1$H-NMR, $^{13}$C-NMR, IR and MS spectra are consistent with the structure.

E) 5-amino-2,4,6-triiodo-1,3-benzenedicarboxylic acid dichloride

A mixture of 1.2 kg of compound D), 6 g of quinoline and 970 g of dodecane is heated at 65°–70° C., with stirring in a nitrogen atmosphere. Then in 2 h, 500–600 g of a mixture of $SOCl_2$/10% n-dodecane are added and then, in 4–6 h, 1 kg of $SOCl_2$ is added keeping the temperature between 65° and 70° C. When the addition is complete the content is heated at 80°–85° C. in 2 h keeping the temperature for 6 h, to complete the reaction. Then the content is cooled to 40°–50° C. and under vacuum the temperature is kept to 80°–85° C. with stirring, distilling a $SOCl_2$/10% n-dodecane mixture, which can be reused.

The pressure is taken to normal values through nitrogen, the content is cooled to a temperature of less than 55° C. and always under nitrogen atmosphere and with stirring, 1.3 kg of diethylenglycol dimethyl ether (diglyme) are added, keeping the temperature between 40° and 50° C.

Then 280–240 g of NaOH are added (13–15% aqueous solution), while the temperature increases to approx. 60° C. with a resulting final pH of 2.5–3. 300 g of water are added and pH is adjusted to 6 by adding 690–590 g of NaOH (13–15% aqueous solution); the mixture is then diluted with 150–180 g of water; at a temperature of 30° C.

The suspension is filtered under nitrogen atmosphere and the wet product washed with water. The product is dried at 50°–65° C., thus giving 1.237 kg of the desired product.

Yield on anhydrous product: 95.6%

Water content: 1%

HPLC: 98.5%

Stationary phase: column E. Merck Lichrospher® RP-18 5 μm 4 mm×12.5 cm

Mobile phase gradient elution

| A | = | water | |
|---|---|---|---|
| B | = | CH$_3$CN | |
| | | min | % B |
| | | 0 | 60 |
| | | 3 | 60 |
| | | 12 | 80 |
| | | 19 | 80 |
| | | 20 | 60 |

Flow: 1.2 ml min$^{-1}$
Temperature: 30° C.
UV detection: 240 nm $^1$H-NMR, $^{13}$C-NMR, IR and MS spectra are consistent with the structure.

F) (S)-5-[[2-(acetyloxy)-1-oxopropyl]amino]-2,4,6-triiodo-1,3-benzenedicarboxylic acid dichloride.

700 g of compound (E) are dissolved, at room temperature and with stirring, in 1 kg of dimethylacetamide and after cooling at 15° C., 15 g of HCl(g) are added. Then 288 g of compound B) are added in 4 h and the temperature is kept between 8°–15° C. The reaction terminates after keeping the solution for 30–40 h at a temperature of 6°–15° C.

488 g of n-butylacetate and 1.28 kg of water are added to the reaction mixture with stirring in 5 min. Then the stirring is stopped for 15 minutes to separate the phases. The lower organic phase is formed by n-butyl acetate, final product and a small amount of dimethylacetamide. After separation, the pH is adjusted at 4 by adding 450 g of 5% NaHCO$_3$ solution. Then 405 g of water are added with stirring obtaining a suspension which is filtered. The wet product is washed with 42.5 g of n-butyl acetate and with 600 g of water in two parts. The same operations are performed on the two remaining parts of the organic phase. The wet final product is dried at a temperature of 55° C., thus giving 755 g of the desired product.

Yield on anhydrous product: 90.0%
Water content: 1%
$[\alpha]_{20}^{D}=-14.2°$ (c=10, CH$_3$CN)
HPLC: 99.2%
Stationary phase: column E. Merck Lichrospher® RP-18 5 μm 4 mm×12.5 cm Mobile phase: gradient elution

| A | = | water | |
|---|---|---|---|
| B | = | CH$_3$CN | |
| | | min | % B |
| | | 0 | 45 |
| | | 3 | 45 |
| | | 9.5 | 45 |
| | | 15 | 100 |
| | | 17 | 45 |

Flow: 1.0 ml min$^{-1}$
Temperature: 30° C.
UV detection: 245 nm $^1$H-NMR, $^{13}$C-NMR, IR and MS spectra are consistent with the structure.

EXAMPLE 2

Preparation of S-(-)-5-[[2-(acetyloxy)-1-oxopropyl]amino]-2,4,6-triiodo-1,3-benzenedicarboxylic acid dichloride in presence of dimethylacetamide hydrochloride (DMAC.HCl)

362 g of S-(-)-[2-(acetyloxy)]propionic acid chloride are dissolved, at a temperature of 15°–17° C. and with stirring, into 657 g of dimethylacetamide (DMAC) and 31 g of DMAC.HCl. Then a solution of 894 g of 5-amino-2,4,6-triiodo-1,3-benzenedicarboxylic acid dichloride in 657 g of DMAC is added to the previous solution in 2 h while keeping the temperature at 17° C. The reaction is completed after 20 h at the temperature of 17° C.

1300 g of n-butyl acetate are added and most of DMAC hydrochloride precipitates. The hydrochloride is removed through filtration.

The extraction and washing operations are carried out in a 45-mm- diameter continuous extraction column equipped with rotating and pulsing plates (LABORTEC TK 40/15), fed as follows:

| plate | flow rate | total quantity |
|---|---|---|
| plate 1 (bottom) n-butylacetate | 4.7 l/h | 7 kg |
| plate 5 solution containing the product | 2.3 l/h | |
| plate 13 K$_2$CO$_3$ 23% w/w solution | 1.2 l/h | 0.48 kg |
| plate 15 (head) washing water | 0.9 l/h | 1.4 kg |

The solutions are fed by 3 dosing impulse-pumps PROMINENT and one peristaltic pump WATSON MARLOW 503U with con 3.2-mm tubing (for n-butylacetate).

The pulsation and rotation rate are set at 60% and 20%. The area of the cross section of the extractor is approx. 16 cm$^2$, which is partly occupied by the stirring system; the average free section is equal to 10 cm$^2$.

The extraction takes 1 h and 30 min at a temperature lower than 30° C., keeping n-butylacetate as continuous phase. The final organic phase is concentrated by distilling first heterogeneous azeotropic mixture H$_2$O/n-butylacetate at 20 Torr and at 27° C. and then only the organic solvent at 35° C. In the final step of the concentration the precipitation of the desired product occurs. After cooling, the product is filtered. After drying 925 g of the desired product are obtained.

Yield on anhydrous product: 87%
HPLC: 99.0%
Chemical-physical characteristics are consistent with those previously described.

EXAMPLE 3

Alternative purification of S-(-)-5-[[2-(acetyloxy)-1-oxopropyl]amino]2,4,6-triiodo-1,3-benzenedicarboxylic acid dichloride.

680 g of S-5-[[2-(acetyloxy)-1-oxopropyl]amino]-2,4,6-triiodo-1,3-benzenedicarboxylic acid solution (prepared according to EXAMPLE 1) are diluted with 550 ml of CH$_3$CCl$_3$. After 15 min stirring at room temperature the solution is cooled at 17°–18° C., and the pH is adjusted at 6–6.2 by adding 30% NaOH solution, keeping a temperature between 20°–25° C. The reaction mixture, which contains NaCl, is diluted with 500 ml of water and kept under stirring for 30 min. The two phases are separated and the organic phase is poured into water at room temperature under stirring with a resulting precipitation of the product. The solution is kept with stirring for 1 h at 20°–23° C. and then is filtered under pressure washing first with CH$_3$CCl$_3$ and then with water. 267 g of the desired product are obtained.

Isolation yield: 95%

The characteristics are consistent with those previously described.

EXAMPLE 4

Alternative purification of S-(-)-5-[[2-(acetyloxy)-1-oxopropyl]amino]-2,4,6-triiodo-1,3-benzenedicarboxylic acid dichloride.

680 g of solution of S-5-[[2-(acetyloxy)-1-oxopropyl]amino]-2,4,6-triiodo-1,3-benzenedicarboxylic (prepared according to EXAMPLE 1) are diluted with 256 g of tBuOH. 1040 g of 7% NaOH solution are dropwise added at 30° C. to pH 4.5–5.5. When the addition terminates the slurry is kept for 1 h under stirring by controlling the pH. The solid is filtered and washed with water. 256 g of the desired product are obtained.

Isolation yield: 89.0%

Chemical-physical characteristics are consistent with those previously described.

EXAMPLE 5

Alternative purification of S-(-)-5-[[2-(acetyloxy)-1-oxopropyl]amino]-2,4,6-triiodo-1,3-benzenedicarboxylic acid dichloride.

680 g of S-5-[[2-(acetyloxy)-1-oxopropyl]amino]-2,4,6-triiodo-1,3-benzenedicarboxylic solution (prepared according to EXAMPLE 1) are dropwise added to a hydroalcoholic solution of 496.4 g 30%wt of tert-butanol at a temperature of 20°–40° C. Simultaneously approx. 612 g of 7% NaOH are added, to keep the pH between 3.5–5.5.

When the dropping terminates the slurry is kept under stirring at pH 3.5–4.5 for 1 h. The solid is filtered, and washed with water. 271 g of the desired product are obtained.

Isolation yield: 95%

Chemical-physical characteristics are consistent with those previously described.

EXAMPLE 6

Following the method of EXAMPLE 4, tBuOH is substituted with 2-BuOH giving 241 g of the desired product.

Isolation yield: 85.0%

Chemical-physical characteristics are consistent with those previously described.

We claim:

1. Process for the preparation of S-(-)-5-[[2-(acetyloxy)-1-oxopropyl]amino]-2,4,6-triiodo-1,3-benzenedicarboxylic acid dichloride of formula (I)

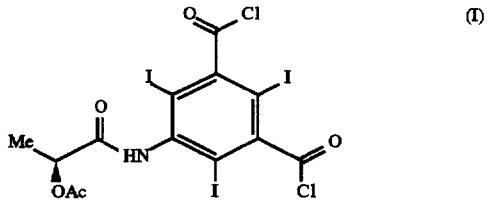

comprising the reaction between S-(-)-[2-(acetyloxy)]propionic acid chloride and 5-amino-2,4,6-triiodo-1,3-benzenedicarboxylic acid dichloride, in an aprotic dipolar solvent and in presence of a halogenhydric acid.

2. The process according to claim 1, in which the halogenhydric acid is added as gas to the solution of 5-amino-2,4,6-triiodo-1,3-benzenedicarboxylic acid dichloride before adding S-(-)-[2-(acetyloxy)]propionic acid chloride.

3. The process according to claim 1, in which the added halogenhydric acid is hydrochloric acid.

4. The process according to claim 3, in which said HCl gas is added in a molar ratio of 0.1–3.

5. The process according to claim 1, in which the aprotic organic solvent is selected in a group consisting of N,N-dimethylacetamide, N,N-dimethylformamide and N-methyl-2-pyrrolidinone, preferably the N,N-dimethylacetamide.

6. The process according to claim 1, in which HCl is added as hydrochloride of dimethylacetamide.

7. The process according to claim 6, in which said hydrochloride of dimethylacetamide is added in a molar ratio of 0.1 to 3.

8. The process according to claim 1, in which the reaction temperature ranges between 0° and 40° C.

9. The process of purification and isolation of S-(-)-5-[[2-(acetyloxy)-1-oxopropyl]amino]-2,4,6-triiodo-1,3benzenedicarboxylic acid dichloride, according to claim 1, comprising the following steps:

the dilution of the reaction mixture with one of the compounds selected from: esters of acetic acid with linear or branched ($C_3$–$C_5$) alcohols or mono-, di- or polychloro ($C_1$–$C_4$) alkanes, in a ratio between the dilution solvent and the aprotic dipolar solvent present in the reaction mixture ranging from 0.3:1 to 2.5:1 w/w;

the extraction with water in a ratio of water to the dilution solvent ranging from 0.5 to 4 w/w;

the precipitation of the product with water.

10. The process of purification and isolation of S-(-)-5-[[2-(acetyloxy)-1-oxopropyl]amino]-2,4,6-triiodo-1,3benzenedicarboxylic acid dichloride, according to claim 9, in which the solvents are selected from propyl acetate, n-butyl acetate and methylchloroform.

11. The process of purification and isolation of S-(-)-5-[[2-(acetyloxy)-1-oxopropyl]amino]-2,4,6-triiodo-1,3-benzenedicarboxylic acid dichloride, according to claim 9, in which the extraction with water is carried out in a continuous extractor fed with the same solvent used for the dilution and with water to the ends and with the mixture diluted on an intermediate plate and the product is isolated by concentration of the solvent phase.

12. The process of purification and isolation of S-(-)-5-[[2-(acetyloxy)-1-oxopropyl]amino]-2,4,6-triiodo-1,3benzenedicarboxylic acid dichloride, according to claim 1, comprising the following steps:

the dilution of the reaction mixture with a ($C_3$–$C_5$) alcohol, linear or branched, in a ratio of dilution solvent to the aprotic dipolar solvent present in the reaction mixture ranging from 0–1.5 w/w;

the precipitation of the product with water.

13. The process of purification and isolation of S-(-)-5-[[2-(acetyloxy)-1-oxopropyl]amino]-2,4,6-triiodo-1,3benzenedicarboxylic acid dichloride, according to claim 1, comprising the following steps:

the addition of the reaction mixture to a hydroalcoholic solution containing a ($C_3$–$C_5$) alcohol, linear or branched, in a ratio of dilution solvent to the aprotic dipolar solvent present in the reaction mixture 0 to 1.5 w/w.

14. The process of purification and isolation of S-(-)-5-[[2-(acetyloxy)-1-oxopropyl]amino]-2,4,6-triiodo-1,3benzenedicarboxylic acid dichloride, according to claim 12, in which the alcohol is selected in a group consisting of isopropanol, tert-butanol and sec-butanol.

15. The process of purification and isolation of S-(-)-5-[[2-(acetyloxy)-1-oxopropyl]amino]-2,4,6-triiodo-1,3- benzenedicarboxylic acid dichloride, according to claim 13, in which the alcohol amount is in a ratio of dilution solvent to the aprotic dipolar solvent present in the reaction mixture ranging from 0.3 to 0.6 w/w.

16. The process of purification and isolation of S-(-)-5-[[2-(acetyloxy)-1-oxopropyl]amino]-2,4,6-triiodo-1,3benzenedicarboxylic acid dichloride, according to claim 9, in which the aprotic dipolar solvent present in the reaction mixture is N,N'-dimethylacetamide.

17. Process for the preparation of S-(-)-5-[[2-(acetyloxy)-1-oxopropyl]amino]-2,4,6-triiodo-1,3-benzenedicarboxylic acid dichloride comprising the following steps:
 a) catalytic hydrogenation of 5-nitro-1,3-benzenedicarboxylic acid in neutral or basic environment, which gives an aqueous solution of 5-amino-1,3-benzenedicarboxylic acid sodium salt;
 b) direct iodination of the 5-amino-1,3-benzenedicarboxylic acid sodium salt solution deriving from step a), without further purification, with a solution of ICl in HCl, being the 5-amino-1,3-benzenedicarboxylic acid sodium salt solution previously added with HCl and $H_2SO_4$ to give 5-amino-2,4,6-triiodo-1,3-benzenedicarboxylic acid;
 c) chlorination of the 5-amino-2,4,6-triiodo-1,3-benzenedicarboxylic acid dichloride, in heterogeneous phase between 5-amino-2,4,6-triiodo-1,3-benzenedicarboxylic acid and thionyl chloride, in a solvent selected from:
 ($C_7$–$C_{16}$) linear or branched hydrocarbons, ($C_7$–$C_8$) aromatic hydrocarbons, 1,1,1-trichloroethane, n-butylacetate, diglyme (diethylenglycoledimethylether), and in the presence of a catalytic amount of a tertiary amine, to give 5-amino-2,4,6-triiodo-1,3-benzenedicarboxylic acid dichloride;
 d) reaction between S-(-)-[2-(acetyloxy)]propionic acid chloride and 5-amino-2,4,6-triiodo-1,3-benzenedicarboxylic acid dichloride, in an aprotic dipolar solvent and in presence of a halogenhydric acid.

* * * * *